United States Patent [19]
Hofheinz et al.

[11] Patent Number: 5,736,557
[45] Date of Patent: Apr. 7, 1998

[54] N,N-BIS (QUINOLIN-4-YL)-DIAMINE DERIVATIVES, THEIR PREPARATION AND THEIR USE AS ANTIMALARIALS

[75] Inventors: Werner Hofheinz, Bottmingen; Werner Leupin, Liestal, both of Switzerland

[73] Assignee: Hoffman-La Roche, Inc., Nutley, N.J.

[21] Appl. No.: 765,751

[22] PCT Filed: Jun. 3, 1995

[86] PCT No.: PCT/EP95/02123

§ 371 Date: Dec. 16, 1996

§ 102(e) Date: Dec. 16, 1996

[87] PCT Pub. No.: WO95/35287

PCT Pub. Date: Dec. 28, 1995

[30] Foreign Application Priority Data

Jun. 17, 1994 [CH] Switzerland ............... 1928/94

[51] Int. Cl.⁶ ............... A61K 31/47; C07D 215/46
[52] U.S. Cl. ............... 514/313; 546/163
[58] Field of Search ............... 546/163; 514/313

[56] References Cited

U.S. PATENT DOCUMENTS

| | | | |
|---|---|---|---|
| 2,816,893 | 12/1957 | Jacob | 260/286 |
| 2,901,484 | 8/1959 | Schock | 260/286 |
| 5,510,356 | 4/1996 | Vennerstrom | 514/313 |

FOREIGN PATENT DOCUMENTS

WO-A-93 07126  4/1996  WIPO.

OTHER PUBLICATIONS

Journal of the Chemical Society, Feb. 1950, pp. 607–611.
Chemical Abstracts, vol. 61, No. 5, Aug. 31, 1964, p. 5668.
Journal of Medicinal Chemistry, vol. 35, No. 11, May 29, 1992, pp. 2129–2134.
Pharmacology & Therapeutics, vol. 57, No. 2/3, Feb. 1993, pp. 203–235.
Biochemistry, vol. 18, No. 22, 1979, pp. 4928–4935.
International Journal of Pharmaceutics, vol. 43, No. 3, May 1988, pp. 215–219.

*Primary Examiner*—C. Warren Ivy
*Assistant Examiner*—Evelyn Huang
*Attorney, Agent, or Firm*—George W. Johnston; Patricia S. Rocha-Tramaloni

[57] ABSTRACT

Disclosed are N,N'-bis(quinolin-4-yl)diamine derivatives of general formula I wherein $R^1$ signifies halogen or trifluoromethyl, $R^2$ signifies hydrogen or halogen, A signifies cyclohexane-1,3-diyl, 2-methyl-cyclohexane-1,3-diyl, cyclohexane-1,4-diyl, dicyclohexylmethane-4,4'-diyl, cyclopentane-1,3-diyl, phenylene-1,4, phenylene-1,3 and phenylene-1,2; n is 1 or 2; m is 1 or 2, as well as their pharmaceutically acceptable salts. These products are useful as agents for preventing malaria and for treating it, especially where the pathogens are resistant to chloroquine.

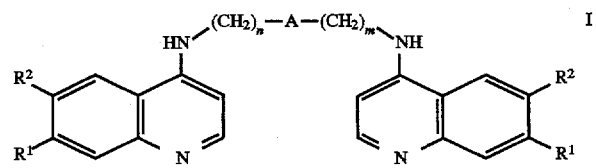

10 Claims, No Drawings

N,N-BIS (QUINOLIN-4-YL)-DIAMINE DERIVATIVES, THEIR PREPARATION AND THEIR USE AS ANTIMALARIALS

This application is the national phase of PCT/EP 95/02123, filed on Jun. 3, 1995, WO 95/35287, published on Dec. 28, 1995.

The invention is concerned with novel diamines, namely N,N'-bis(quinolin-4-yl)-diamine derivatives of the general formula

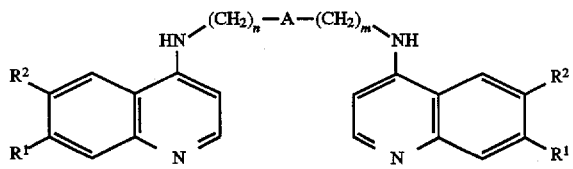

wherein $R^1$ signifies halogen or trifluoromethyl, $R^2$ signifies hydrogen or halogen, A signifies cyclohexane-1,3-diyl, 2-methyl-cyclohexane-1,3-diyl, cyclohexane-1,4-diyl, dicyclohexylmethane-4,4'-diyl, cyclopentane-1,3-diyl, phenylene-1,4, phenylene-1,3, phenylene-1,2, ethene-1,2-diyl or ethyne-1,2-diyl and n and m can be the same or different and signify 0, 1 or 2, as well as their pharmaceutically acceptable salts.

These novel compounds have very good activities against not only chloroquine-sensitive, but also against chloroquine-resistant malaria pathogens. For this reason they are very well suited for preventing malaria and for treating it, especially where the pathogens are resistant to chloroquine.

Objects of the present invention are the novel bis-quinoline derivatives of general formula I as well as pharmaceutically usable salts thereof per se and as pharmaceutically active substances, the manufacture of these compounds and salts, medicaments containing a compound of formula I or a pharmaceutically acceptable acid addition salt thereof, the production of such medicaments and the use of the compounds of formula I and their pharmaceutically acceptable salts in the control or prevention of illnesses, especially of malaria, and, respectively, for the production of such medicaments.

In formula I $R^1$ preferably signifies chlorine, A preferably signifies cyclohexane-1,3-diyl, 2-methyl-cyclohexane-1,3-diyl, cyclohexane-1,4-diyl, dicyclohexylmethane-4,4'-diyl, cyclopentane-1,3-diyl, phenylene-1,4, phenylene-1,3 or phenylene-1,2 and n and m preferably signify 0 or 1.

Compounds of formula I in which $R^1$ signifies chlorine, A signifies ethene-1,2-diyl and n and m signify 1 are also preferred.

Particularly preferred compounds of general formula I are:

(7-Chloroquinolin-4-yl)-[2-(7-chloroquinolin-4-yl-aminomethyl)-benzyl]-amine, (7-chloroquinolin-4-yl)-[3-(7-chloroquinolin-4-yl-aminomethyl)-benzyl]-amine (7-chloroquinolin-4-yl)-[4-(7-chloroquinolin-4-yl-aminomethyl)-benzyl]-amine, ±-trans-N,N'-bis-(7-chloroquinolin-4-yl)-cyclohexane-1,4-diamine, cis-N,N'-bis-(7-chloroquinolin-4-yl)-cyclohexane- 1,4-diamine, cis-N,N'-bis-(7-chloroquinolin-4-yl)-cyclohexane- 1,3-diamine, ±-trans-N,N'-bis-(7-chloroquinolin-4-yl)-cyclohexane-1,3-diamine, cis,cis-N,N'-bis-(7-chloroquinolin-4-yl)-2-methyl-cyclohexane-1,3-diamine, N,N'-bis-(7-chloroquinolin-4-yl)-phenylene-1,3-diamine, cis-N,N'-bis-(7-chloroquinolin-4-yl)-cyclopentane-1,3-diamine, (7-chloroquinolin-4-yl)-[3-(7-chloroquinolin-4-yl-aminomethyl)-cyclohexylmethyl]-amine, N,N'-bis(7-chloroquinolin-4-yl)-dicyclohexylmethane-4,4'-diamine and N,N'-bis-(7-chloroquinolin-4-yl)-2-butene-1,4-diamine.

The novel compounds of formula I can be manufactured in accordance with the invention by a) reacting a compound of the general formula

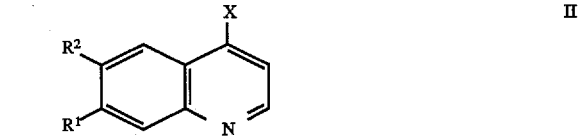

wherein $R^1$ and $R^2$ have the significance set forth above and X signifies a leaving group, with a diamine of the general formula

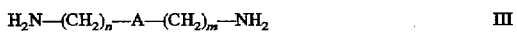

wherein n, m and A have the significance set forth above, or an acid addition salt thereof, and b) if desired, converting the compound obtained into a pharmaceutically acceptable acid addition salt.

Bis-quinoline derivatives of general formula I are manufactured according to variant a) of the process in accordance with the invention by reacting a corresponding compound of general formula II with the corresponding diamines of general formula III. α,α'-Diamino-o-xylene, α,α'-diamino-m-xylene, α,α'-diamino-p-xylene, ±-trans-cyclohexane-1,4-diamine, cis-cyclohexane-1,4-diamine, cis-cyclohexane-1,3-diamine, ±-trans-cyclohexane-1,3-diamine, cis,cis-2-methyl-cyclohexane-1,3-diamine, phenylene-1,3-diamine, cis-cyclopentane-1,3-diamine, 1,3-bis-(aminomethyl)-cyclohexane, 4,4'-diamino-dicyclohexylmethane or trans-2-butene-1,4-diamine can be used, for example, as the diamine. In place of the free diamines, their acid addition salts can also be used.

Suitable compounds of formula II are, for example, 4,7-dichloroquinoline or 4-chloro-7-trifluoromethyl-quinoline.

The reaction is conveniently effected under a protective gas atmosphere in a temperature range of 100°–200° C. and in a solvent, with phenol, N-methyl-2-pyrrolidone, N,N-dimethylacetamide, ethoxyethanol or acetonitrile being preferred. The presence of a tertiary amine such as triethylamine influences the reaction favourably, but is not essential. When the acid addition salt of a diamine is used, the presence of a tertiary amine such as triethylamine is required. The reaction time can vary between 2 and 28 hours.

The conversion into a pharmaceutically acceptable acid addition salt according to process variant b) is conveniently effected by adding an acid. Hydrochloric acid, methanesulphonic acid or acetic acid is especially preferred because of the physiological compatibility of the corresponding salts. Convenient solvents which are especially suitable are: water, methanol, ethanol, isopropanol, diethyl ether, N,N-dimethylformamide or dioxan.

The diamines and quinoline derivatives which are required as starting materials for process variant a) are commercial products or can be prepared according to methods known per se.

As mentioned earlier, the bis-quinoline derivatives of general formula I in accordance with the invention and their pharmaceutically usable salts have extremely valuable pharmacological properties.

The following Tables 1–3 show their activity against not only chloroquine-resistant, but also chloroquine-sensitive malaria pathogens.

Test Method for the Determination of the Activity Against *Plasmodium falciparum* in vitro The preparations are tested on intraerythrocytary stages of *Plasmodium falciparum* from asynchronous cultures according to the method of Desjardin et al. (Desjardins, R. E. et al: Quantitative assessment of antimalarial activity in vitro by a semiautomated microdilution technique. Antimicrob. Agents Chemother. 16, 710–718, (1979)).

The culture medium consists of RPMI 1640 with the addition of 25 mM HEPES, 25 mM NaHCO$_3$, 100 µg/ml neomycin and 105 human serum (A$^+$). Human-A$^+$ erythrocytes are used as the *Plasmodium falciparum* host cells. The parasites are maintained at 37° C. in an atmosphere of 3% O$_2$, 4% CO$_2$, 9:3% N$_2$ and 95% relative humidity.

In order to determine the activity, the preparations are dissolved in dimethyl sulphoxide, pre-diluted in the culture medium to a suitable starting concentration and subsequently titrated-out on to microtitre plates in the 2nd stage over 6–7 steps. After the addition of the parasite culture (0.7% parasitemia in 2.5% erythrocyte suspension) the test plates are incubated under the conditions given above for 48 h–72 h. The parasite growth in the different preparation concentrations is determined using [G—$^3$H]-hypoxanthin incorporation compared to untreated control cultures on the same test plates. The 50% growth inhibition (IC$_{50}$) is calculated according to logit regression analysis from the resulting dosage-activity curve.

The preparations are tested on at least one chloroquine-resistant and one chloroquine-sensitive *Plasmodium falciparum* strain. Additional sensitive and resistant strains are included for futher characterization.

Test Method for the Determination of the Activity Against *Plasmodium berghei* in vivo The preparations are tested on mice infected with malaria pathogens (*Plasmodium berghei*). Male albino mice (IBM:MORO(SPF), FUELLINSDORF) weighing about 25 g are used as the test animals. They are kept in climatized rooms at 21°–22° C. in groups of 5 animals per cage. They receive ad libitum a diet feed with a low PABA content (NAFAG FUTTER © No. 9009 PAB-45, PABA content 45 mg/kg) and drinking water. On the first day of the test (D0) the test animals are infected with *Plasmodium berghei* (strain ANKA). For this there is used heparinized blood of a donor mouse with about 30% parasitemia, which is diluted with physiological saline such that it contains 10$^8$ parasitized erythrocytes per ml. 0.2 ml of this suspension is injected intravenously (i.v.) into the mice to be treated and into the control mice. In untreated control animals the parasitemia normally reaches 30–40% on the third day after the infection (D+3) and the test animals die between days +5 and +7.

The substances to be tested are dissolved or suspended in distilled water or in a mixture of 7% Tween 80, 3% alcohol (96%) and water. Usually, 0.25 ml of this solution or suspension is administered once subcutaneously and per-orally to groups of 5 test animals. Treatment is effected 24 hours after the infection. 10 control animals are treated in the same manner with solvent or suspension medium per test.

All substances are tested in a first test in a single dosage of 10 mg/kg. Only those substances which in this test (10 mg/kg) have shown a parasitaemia reduction of 90% are used for the titration. Suitable dilutions of the test substance can be used to obtain an accurate titration of the activity.

48 hours after the treatment (D+3) blood smears are prepared from all animals using blood from tail veins and are stained with giemsa. The average erythrocyte infection rate (parasitemiea in %) in the control groups as well as in the groups which have been treated with the test compounds is determined by counting under a microscope. The difference in the average values of the infection rates of control group (100%) and treated groups is calculated and expressed as a percentage reduction (GI%). The ED$_{50}$ or ED$_{90}$ is determined mathematically by means of the JMP programme (nonlinear fit). The ED$_{50}$ (ED$_{90}$) in mg/kg is that dose which after single administration reduces the average erythrocyte infection rate by 50% (90%) in comparison to the control group.

TABLE 1

Values measured in vitro for the growth inhibition of chloroquine-sensitive strains of the human-pathogenenic *Plasmodium falciparum* (IC$_{50}$ values in ng/ml)

| Example | NF54 | FCH5C2 | HB3 | RFMEF3 | Ro73 |
|---|---|---|---|---|---|
| 1 | 10.2 | 6.6 | 7.5 | 6.5 | 3.6 |
| 2 | 10.3 | 12.5 | 8.9 | 7.8 | 13.3 |
| 3 | 9.6 | 12.7 | 4.6 | 12.5 | 7.4 |
| 4 | 7.2 | 3.6 | 3.3 | 3.3 | 1.6 |
| 5 | 2.6 | 3.9 | 3.2 | 3.4 | 2.3 |
| 6 | 3.8 | 6.4 | 5.2 | 4.8 | 3.0 |
| 7 | 10.7 | | | | |
| 8 | 7.7 | 6.1 | 6.1 | 6.3 | 1.6 |
| 9 | 23.7 | 15.6 | 9.5 | 10.8 | 10.4 |
| 11 | 17.2 | 14.5 | 12.7 | 16.8 | 4.9 |
| 12 | 11.6 | 19.4 | 26.3 | 13.7 | 17.8 |
| 13 | 30.8 | | | | |
| Chloroquine | 7.6 | 12.2 | 11.3 | 14.2 | 8.0 |

TABLE 2

Value measured in vitro for the growth inhibition of chloroquine-resistant strains of the human-pathogenic *Plasmodium falciparum* (IC$_{50}$ values in ng/ml) and the ratio of average IC$_{50}$ values for resistant strains and average values for sensitive strains as a measurement of resistance towards the test substance ("resistance index").

| Example | RFCF3 | ItG2F6 | Indo | K1 | W2 | 7G8 | W2 Mef | Resistance index |
|---|---|---|---|---|---|---|---|---|
| 1 | 5.4 | 4.7 | 6.9 | 6.9 | 5.8 | 7.0 | 4.9 | 0.9 |
| 2 | 26.3 | 19.0 | 15.8 | 17.0 | 100.0 | 13.9 | 17.0 | 2.8 |
| 3 | 5.7 | 7.9 | 2.9 | 9.1 | 5.0 | 6.8 | 9.7 | 0.7 |
| 4 | 9.5 | 5.3 | 6.0 | 11.6 | 13.1 | 2.8 | 7.0 | 2.1 |

TABLE 2-continued

Value measured in vitro for the growth inhibition of chloroquine-resistant strains of the human-pathogenic *Plasmodium falciparum* ($IC_{50}$ values in ng/ml) and the ratio of average $IC_{50}$ values for resistant strains and average values for sensitive strains as a measurement of resistance towards the test substance ("resistance index").

| Example | RFCF3 | ItG2F6 | Indo | K1 | W2 | 7G8 | W2 Mef | Resistance index |
|---|---|---|---|---|---|---|---|---|
| 5 | 5.1 | 6.8 | 4.4 | 7.7 | 4.8 | 9.0 | 6.5 | 2.1 |
| 6 | 4.2 | 4.1 | 3.0 | 4.4 | 4.0 | 3.8 | 7.6 | 1.0 |
| 7 | | | | 10.5 | | | | |
| 8 | 4.6 | 6.4 | 6.4 | 8.8 | 5.6 | 9.4 | 9.1 | 1.3 |
| 9 | 12.5 | 12.9 | 7.7 | 17.1 | 12.1 | 17.1 | 12.1 | 0.9 |
| 11 | 14.1 | 11.6 | 14.4 | 17.8 | 9.9 | 20.5 | 15.9 | 1.1 |
| 12 | 7.2 | 13.3 | 13.7 | 13.0 | 25.0 | 17.1 | 21.6 | 0.9 |
| 13 | | | | 18.1 | | | | |
| Chloroquine | 130.0 | 68.0 | 52.0 | 114.0 | 123.0 | 81.0 | 79.0 | 8.7 |

TABLE 3

Activity measured in vivo against *Plasmodium berghei* in mice. GI % is the percentage parasitemia reduction after single, perorally (po) or subcutaneously (sc) administered dose of 10 mg/kg of test substance; $ED_{50}$ is the effective perorally administered dose of test substance

| Example | GI % at 10 mg/kg po | GI % at 10 mg/kg sc | $ED_{50}$ po mg/kg |
|---|---|---|---|
| 1 | 62.0 | 97.0 | |
| 2 | 87.0 | 99.0 | |
| 3 | 99.9 | 99.9 | 2.5 |
| 4 | 73.0 | 37.0 | |
| 5 | 98.0 | 99.9 | 1.5 |
| 6 | 98.0 | 99.9 | 1.7 |
| 7 | 97.0 | 99.0 | |
| 8 | 66.0 | 67.0 | |
| 9 | 86.0 | 83.0 | |
| 11 | 28.0 | 99.6 | |
| Chloroquine | 99.9 | 99.9 | 2.0 |

The compounds of formula I and the pharmaceutically acceptable acid addition salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and the pharmaceutically acceptable acid addition salts of the compounds of formula I can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active ingredient no carriers are, however, usually required in the case of soft gelatine capsules. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

Medicaments containing a compound of formula I or a pharmaceutically acceptable acid addition salt thereof and a therapeutically inert carrier are also an object of the present invention, as is a process for their manufacture which comprises bringing one or more compounds of formula I and/or pharmaceutically acceptable acid addition salts thereof and, if desired, one or more other thereapeutically valuable substances into a galenical administration form together with one or more therapeutically inert carriers.

In accordance with the invention compounds of general formula I as well as their pharmaceutically acceptable acid addition salts can be used for the treatment or prevention of malaria and, respectively, for the production of corresponding medicaments. The dosage can vary within wide limits and will, of course, be fitted to the individual requirements in each particular case. In the case of oral administration the dosage lies in a range of about 10 mg to about 2.5 g per day of a compound of general formula I or the corresponding amount of a pharmaceutically acceptable acid addition salt thereof, although the upper limit can also be exceeded when this is found to be indicated.

In the following Examples, which illustrate the present invention but are not intended to limit its scope in any manner, all temperatures are given in degrees Celsius. The 250 MHz—$^1$H—NMR spectra were measured at room temperature; chemical shifts δ(ppm) relative to δ(TMS)=0.0 ppm.

EXAMPLE 1

(7-Chloroquinolin-4-yl)-[2-(7-chloroquinolin-4-yl-aminomethyl)-benzyl]-amine 2.67 g of 4,7-dichloroquinoline, 1.47 g of α,α'-diamino-o-xylene dihydrochloride and 3.8 ml of triethylamine are reacted at 140° C. under argon for 5 hours. After cooling 100 ml of 2N NaOH and 100 ml of ethyl acetate are added, a small amount (0.68 g) of insoluble crystalline product is filtered off and the organic phase is separated. The residue remaining after evaporation of the solvent is combined with the filtered-off crystals and recrystallized from 25 ml of methanol. There is obtained 0.45 g of the amine as a colourless product which is dissolved in 5 ml of hot methanol. The dimethanesulphonate crystallizes out after the addition of 0.13 ml of methanesulphonic acid. There is obtained 0.56 g, m.p.:>250° C.

Elementary analysis: $C_{26}H_{20}Cl_2N_4 \cdot 2(CH_3SO_3H) \cdot 0.5\ H_2O$
Calculated:: C 51.35%, H 4.39%, Cl 10.64%, N 8.40%, S 9.62%
Found: C 51.14%, H 4.32%, Cl 10.68%, N 8.20%, S 9.64%

EXAMPLE 2

(7-Chloroquinolin-4-yl)-[3-(7-chloroquinolin-4-yl-aminomethyl)-benzyl]-amine 3.96 g of 4,7-dichloroquinoline and 1.36 g of α,α'-diamino-m-xylene are reacted at 140° C. in 4 g of phenol under argon for 24 hours. After cooling the mixture is treated with 20 ml of ethyl acetate and 30 ml of water and adjusted to pH 1 by adding a small amount of concentrated hydrochloric acid. The product which thereby crystallizes out is filtered off under suction and triturated in 200 ml of 2N NaOH and 50 ml of ethyl acetate. The separated crystalline amine is suspended in 80 ml of 0.5N HCl and brought into solution on a steam bath by the addition of ethanol (75 ml). 3.14 g of the dihydrochloride crystallize out upon cooling, m.p.:>250° C.

Elementary analysis: $C_{26}H_{20}Cl_2N_4 \cdot 2HCl \cdot H_2O$
Calculated:: C 56.75%, H 4.40%, Cl 25.77%, N 10.18%
Found: C 56.54%, H 4.23%, Cl 25.79%, N 09.89%

$^1$H—NMR in DMSO-d$_6$, δ(ppm):3.35(s,2H [H$_2$O]), 4.79 (d, 4H, J=6 Hz), 6.58(d, 2H, J=7.5 Hz), 7.24(s,1H), 7.37 (m, 3H), 7.69(dd, 2H, J=2.5 and 9 Hz), 8.04(d,2H, J=2.5 Hz), 8.38(d, 2H, J=7.5 Hz), 8.59(d, 2H, J=9 Hz), 10.23(t, 2H, J=6Hz).

EXAMPLE 3

(7-Chloroquinolin-4-yl)-[4-(7-chloroquinolin-4-yl-aminomethyl)-benzyl]-amine 2.9 g of 4,7-dichloroquinoline, 1 g of α,α'-diamino-p-xylene and 1.3 g of triethylamine are reacted at 120° C. in 10 ml of ethoxyethanol under argon for 16 hrs. After cooling 40 ml of water and 40 ml of ethyl acetate are added and the mixture is adjusted to pH 1 by means of concentrated hydrochloric acid. The product which thereby separates is triturated in 150 ml of 2N NaOH with the addition of 100 ml of ethyl acetate, 0.8 g of crystalline amine being obtained. 0.84 g of crystalline dihydrochloride, m.p.:>250° C., is obtained therefrom by boiling in 15 ml of 1N HCl and 10 ml of ethanol.

Elementary analysis: $C_{26}H_{20}Cl_2N_4 \cdot 2HCl$
Calculated:: C 58.67%, H 4.17%, Cl 26.64%, N 10.53%
Found: C 56.40%, H 4.22%, Cl 26.93%, N 10.38%

$^1$H—NMR in DMSO-d$_6$+D$_2$O, δ(ppm):4.57(s, 4H), 5.54 (d, 2H, J=7.5 Hz), 7.26(s, 1H), 7.56(dd, 2H, J=2 and 9 Hz), 7.75(d, 2H, J=2 Hz), 8.15(d, 2H, J=7.5 Hz), 8.23(d, 2H, J=9 Hz)

EXAMPLE 4

±-trans-N,N'-Bis-(7-chloroquinolin-4-yl)-cyclohexane-1,4-diamine

Analogously to Example 3, from 2.28 g of ±trans-cyclohexane-1,4-diamine and 7.92 g of 4,7-dichloroquinoline there are obtained 2 g of the dihydrochloride; colourless crystals from methanol-water, m.p.:>250° C.

Elementary analysis: $C_{24}H_{22}Cl_2N_4 \cdot 2HCl$
Calculated:: C 56.49%, H 4.74%, Cl 27.79%, N 10.98%
Found: C 56.51%, H 4.63%, Cl 28.03%, N 10.98%

EXAMPLE 5 cis-N,N'-Bis-(7-chloroquinolin-4-yl)-cyclohexane-1,4-diamine

The dihydrochloride, colourless crystals from methanol-water, m.p.:>260° C., is obtained analogously to Example 3 from cis-cyclohexane-1,4-diamine and 4,7-dichloroquinoline.

Elementary analysis: $C_{24}H_{22}Cl_2N_4 \cdot 2HCl$
Calculated:: C 56.49%, H 4.74%, Cl 27.79%, N 10.98%
Found: C 56.76%, H 4.73%, Cl 27.57%, N 10.83%

$^1$—HMR in DMSO-d$_6$;δ(ppm):1.86(m, 4H); 2.00(m, 4H); 3.81(m, 2H); 6.63(d, 2H); 7.14(d, 2H); 7.50(dd, 2H); 7.82(d, 2H); 8.44(d, 2H); 8.48(d, 2H).

EXAMPLE 6 cis-N,N'-Bis-(7-chloroquinolin-4-yl)-cyclohexane-1,3-diamine 23.2 g of cis-cyclohexane-1,3-diamine and 80.5 g of 4,7-dichloroquinoline are reacted at 150° C. in 400 ml of N-methyl-2-pyrrolidone under argon for 24 hours. After cooling insoluble material is filtered off and the filtrate is treated with 600 ml of water. The separated crude product is introduced into 400 ml of water and 100 ml of glacial acetic acid. The mixture is extracted three times with 200 ml of ethyl acetate each time and then adjusted to pH 12 by the addition of 600 ml of 2N NaOH. The separated crystalline diamine is recrystallized from 270 ml of dimethylformamide, 20.1 g of pure product being obtained. This is converted into the dimethanesulphonate in 200 ml of boiling acetonitrile with 6.4 ml of methanesulphonic acid. 19.5 g of colourless crystalline salt, m.p.:>250° C., are obtained.

Elementary analysis: $C_{24}H_{22}Cl_2N_4 \cdot 2(CH_3SO_3H)$
Calculated:: C 49.60%, H 4.80%, Cl 11.26%, N 8.90%, S 10.18%
Found: C 49.50%, H 5.00%, Cl 11.34%, N 8.77%, S 10.21%

$^1$H—NMR in DMSO-d$_6$+D$_2$O,δ(ppm):1.6–2.45(multiple m, 8H), 2.52 (s, 6H), 4.15 (m, 2H), 7.08(d, 2H, J=7.5 Hz), 7.76(dd, 2H, J=2 and 8.5 Hz), 7.94(d, 2H, J=2 Hz), 8.46(d, 2H, J=7.5 Hz), 8.56(d, 2H, J=8.5 Hz

EXAMPLE 7

±-trans-N,N'-Bis-(7-chloroquinolin-4-yl)-cyclohexane-1,3-diamine

Analogously to Example 6, from 8.5 g of ±-trans-cyclohexane-1,3-diamine bis-trifluoroacetate, 10.1 g of triethylamine and 9.9 g of 4,7-dichloroquinoline there are obtained 1.6 g of pure diamine. This is dissolved in 16 ml of hot isopropanol. The dihydrochloride crystallizes out after the addition of 1.6 ml of 4.8N isopropanolic hydrochloric acid. 1.04 g of colourless crystallizate are obtained, m.p.:>250°.

$^1$H—NMR in DMSO-d$_6$+D$_2$O,δ(ppm): 1.84(broad m, 6H), 2.24(m, 2H), 4.52 (m, 2H), 7.02(d, 2H, J=7.5 Hz), 7.78(dd, 2H, J=2 und 9.5 Hz), 8.02(d, 2H, J=2 Hz), 8.55(d, 2H, J=7.5 Hz), 8.86(d, 2H, J=9.5 Hz)..

EXAMPLE 8 cis,cis-N,N'-Bis-(7-chloroquinolin-4-yl)-2-methyl-cyclohexane-1,3-diamine

Analogously to Example 3, from 3.36 of cis,cis-2-methyl-cyclohexane-1,3-diamine dihydrochloride, 10.38 g of 4,7-dichloroquinoline and 5.3 g of triethylamine there are obtained 1.23 g of pure diamine. From a hot solution in 10 ml of glacial acetic acid there crystallize, after the addition of 0.7 ml of methanesulphonic acid, 1.23 g of colourless dimethanesulphonate which is recrystallized from methanol; m.p.:>250° C.

Elementary analysis: $C_{25}H_{24}Cl_2N_4 \cdot 2(CH_3SO_3H)$
Calculated:: C 50.39%, H 5.01%, Cl 11.02%, N 8.71%, S 09.96%
Found: C 50.28%, H 4.97%, Cl 11.11%, N 8.53%, S 10.03%

$^1$H—NMR in DMSO-$d_6$,δ(ppm): 0.90(d, 3H, J=6 Hz), 1.5–2.2 (multiple m, 6H), 2.44(s, 6H), 2.64(m, 1H), 4.402 (m, 2H), 7.44(d, 2H, J=8 Hz), 7.80(dd, 2H, J=2 and 9.5 Hz), 7.97(d, 2H, J=2 Hz), 8.62 (d, 2H, J=8 Hz), 8.80(d, 2H, J=9.5 Hz), 8.87(d, 2H, J=8 Hz), 13.9(breit, 2H).

EXAMPLE 9

N,N'-Bis-(7-Chloroquinolin-4-yl)-phenylene-1,3-diamine 0.54 g of phenylene-1,3-diamine and 2 g of 4,7-dichloroquinoline are dissolved in 20 ml of 1-methyl-2-pyrrolidone and heated to 140° C. while stirring for 16 hours. After cooling the reaction solution is added to 60 ml of ethyl acetate. The crystals which thereby separate are filtered off under suction and recrystallized from HCl-saturated methanol solution. There is obtained 0.77 g:m.p.:>280° C.

Elementary analysis: $C_{24}H_{16}Cl_2N_4 \cdot 2(HCl)$
Calculated:: C 57.17%, H 3.60%, Cl 28.12%, N 11.11%
Found: C 57.08%, H 3.61%, Cl 27.98%, N 10.90%

$^1$H—NMR in DMSO-$d_6$,d (ppm):7.04(d, 2H); 7.51(dd, 2H); 7.59(d, 1H); 7.75 (t, 1H); 7.90(dd, 2H); 8.10(d, 2H); 8.63(d, 2H); 8.78(d, 2H); 10.92(s, 2H).

EXAMPLE 10 cis,N,N'-Bis-(7-chloroquinolin-4-yl)-cyclopentane-1,3-diamine 3.6 g of pure diamine are obtained from 2.62 g of cis-cyclopentane-1,3-diamine, 4 g of 4,7-dichloroquinoline and 2 g of triethylamine analogously to Example 6. 2.5 g of di-methanesulphonate, m.p.:>25° C., crystallize from a solution of 2 g of the base in 20 ml of glacial acetic acid upon adding 0.5 ml of methanesulphonic acid and 20 ml of diethyl ether.

Elementary analysis: $C_{23}H_{20}Cl_2N_4 \cdot 2(CH_3SO_3H)$
Calculated:: C 48.78%, H 4.59%, Cl 11.52%, N 9.10%, S 10.42%
Found: C 48.62%, H 4.37%, Cl 11.13%, N 8.86%, S 10.23%

$^1$H—NMR in DMSO-$d_6$,δ(ppm): 1.95–2.3 (multiple m, 5H), 2.39(s, 6H), 2.85(m, 1H), 4.42(m, 2H), 7.01(d, 2H, J=7.5 Hz), 7.81(dd, 2H, J=2 and 9 Hz), 7.97(d, 2H, J=2 Hz), 8.62(d, 2H, J=7.5 Hz), 8.74(d, 2H, J=9 Hz), 9.16(d, 2H, J=8 Hz), 13.87(broad, 2H).

EXAMPLE 11

(7-Chloroquinolin-4-yl)-[3-(7-chloroquinolin-4-yl-aminomethyl)-cyclohexylmethyl]-amine Analogously to Example 3, from 10 g of 1,3-bis-(aminomethyl)-cyclohexane, 27.9 g of 4,7-dichloroquinoline and 19.6 g of triethylamine there are obtained 6.8 g of crystalline diamine. This is converted in 175 ml of methanol using 4.9 ml of methanesulphonic acid into the di-methanesulphonate which is recrystallized from 43 ml of water, 17 ml of acetone and 175 ml of diethyl ether. There are obtained 5.6 g of colourless crystalline product, m.p.:92–95° C.

Elementary analysis: $C_{26}H_{26}Cl_2N_4 \cdot 2.2(CH_3SO_3H)$
Calculated:: C 50.05%, H 5.18%, Cl 10.48%, N 8.28%, S 10.42%
Found: C 50.15%, H 5.36%, Cl 10.70%, N 8.34%, S 10.16%

EXAMPLE 12

N,N'-Bis-(7-chloroquinolin-4-yl)-dicyclohexylmethane-4,4'-diamine 6.3 g of colourless, crystalline dihydrochloride, m.p.:>250° C., are obtained from 4.2 g of 4,4'-diaminodicyclohexylmethane and 7.92 g of 4,7-dichloroquinoline.

Elementary analysis: $C_{31}H_{34}Cl_2N_4 \cdot 2HCl \cdot 0.5H_2O$
Calculated:: C 59.62%, H 6.13%, Cl 22.71%, N 8.97%
Found: C 59.60%, H 5.86%, Cl 23.22%, N 9.05%

EXAMPLE 13

N,N'-Bis-(7-chloroquinolin-4-yl)-2-butene-1,4-diamine

In analogy to Example 6, from 1.6 g of trans-2-butene-1,4-diamine dihydrochloride, 4 g of 4,7-dichloroquinoline and 4 g of triethylamine there are obtained 1.5 g of the base. This is converted into the bis-methanesulphonate by adding 0.5 ml of methanesulphonic acid to a boiling solution in 28 ml of methanol and 12 ml of glacial acetic acid. There is obtained 0.86 g of colourless crystals, m.p.:>250° C.

Elementary analysis: $C_{22}H_{20}Cl_2N_4 \cdot 2(CH_3SO_3H)$
Calculated:: C 47.92%, H 4.36%, Cl 11.79%, N 9.31%, S 10.66%
Found: C 47.98%, H 4.36%, Cl 11.77%, N 9.15%, S 10.58%

$^1$H—NMR in DMSO-$d_6$,δ(ppm):2.41(s, 6H), 4.24(s, broad, 4H), 5.86(s, broad, 2H), 6.83(d, 2H, J=7.5 Hz), 7.79(dd, 2H, J=2 and 9 Hz), 7.98(d, 2H, J=2 Hz), 8.52(d, 2H, J=9 Hz), 8.56(d, 2H, J=7.5 Hz), 9.63(t, 2H), 13.85(broad, 2H).

The intermediates used in the foregoing Examples, insofar as they are not commercially available, can be prepared in the following manner:

EXAMPLE 14

α,α'-Diamino-ortho-xylene (see Example 1)

12.3 g of α,α'-dibromoxylene and 17.3 g of potassium phthalimide are stirred in 390 ml of N,N- dimethylformamide at a bath temperature of 150° C. for 2.4 hours. After cooling the resulting intermediate is filtered off under suction, washed with ethyl acetate, dried and then reacted in 200 ml of ethanol with 4.6 ml of hydrazine hydrate under reflux. After cooling the resulting suspension is treated with 50 ml of 25% hydrochloric acid, filtered and concentrated to ⅓ of its volume. After repeated filtration the mixture is adjusted to pH 14 by the addition of concentrated sodium hydroxide solution and evaporated. The product is dissolved out from the residue with 300 ml of methylene chloride. After evaporation of the solvent the residue as is taken up in 25 ml of isopropanol and the dihydrochloride of the product is crystallized with 20 ml of 3.26N isopropanolic hydrochloric acid. There are obtained 2.64 g, colourless crystals; m.p.:>250° C.

$^1$H—NMR in DMSO-d$_6$,δ(ppm):4.16(s, 4H), 7.44(m, 2H), 7.50(m, 2H), 8.67(s, 6H)

EXAMPLE 15

±-trans-Cyclohexyl-1,3-diamine and cis-cyclohexyl-1,3-diamine (see Examples 6 and 7)

50 g of phenylene-1,3-diamine in 508 ml of 1N NaOH are treated with 222 g of di-tert.-butyl dicarbonate dissolved in 500 ml of dioxan. The mixture is stirred at RT for 24 hours and thereafter evaporated in a vacuum. 700 ml of water are added to the residue and the mixture is adjusted to pH 1 with conc. hydrochloric acid and extracted 5 times with 500 ml of ethyl acetate each time. After evaporation of the solvent the residue is recrystallized from 1200 ml of hexane and 850 ml of tert.-butyl methyl ether. 88.1 g of bis-BOC derivative, m.p.:145°–148° C., are obtained. This is hydrogenated on 30 g of Rh/C in 4 l of methanol at 50 bar and 65° C. After filtering off from the catalyst the solvent is removed in a vacuum and the residue is recrystallized from 1800 ml of methanol. There is obtained a first crystal fraction of 33 g and, after concentration of the filtrate to about 800 ml, a second crystal fraction of 5.6 g. A further 14.4 g are obtained after boiling the filtered-off catalyst residue with 900 ml of methanol. The three crystallizates consist of pure cis-N,N'-bis-BOC-cyclohexane-1,3-diamine; m.p.:232° C. (dec.); total 53 g.

From the mother liquor of the above crystallization there are obtained, after evaporation and recrystallization from 160 ml of hexane and 17 ml of ethyl acetate, 10 g of trans-N,N'-bis-BOC-cyclohexane-1,3-diamine as colourless crystals: m.p.:131°–132° C.

cis-Cyclohexane-1,3-diamine: 93.4 g of the BOC-derivative are introduced into 500 ml of trifluoroacetic acid while cooling with ice. After stirring at RT for 4 hours the trifluoroacetic acid is evaporated, the residue is dissolved in 200 ml of water, concentrated sodium hydroxide solution is added until the pH has reached 14 and the mixture is again evaporated to dryness. The cis-cyclohexane-1,3-diamine is then taken up with 500 ml of dichloromethane and, after evaporation of the solvent, is isolated as an oil (23.2 g).

$^1$H—NMR in DMSO-d$_6$,δ(ppm):0.70–0.91(m, 3H), 1.14 (m, 1H), 1.57(m, 1H), 1.67(m, 2H), 1.84(m; 1H), 2.5(m, 2H)

±-trans-Cyclohexane-1,3-diamine: 22.9 g of the BOC derivative are introduced into 1 00 ml of trifluoroacetic acid while cooling with ice. The mixture is left at RT for 4 hours, evaporated and the residue is recrystallized from 200 ml of acetonitrite. 8.5 g of ±-trans-cyclohexane-1,3-diamine trifluoroacetate, m.p. 200° C. (sintering) are obtained.

$^1$H—NMR in DMSO-d$_6$,δ(ppm):1.5–1.8(m, 6H), 1.88(t, 2H), 3.49(m, 2H)

EXAMPLE 16 cis,cis-2-Methyl-cyclohexane-1,3-diamine (see Example 8)

cis,cis-2-Methyl-cyclohexane-1,3-diamine is obtained as an oil in analogy to Example 15 from 2,6-diaminotoluene after conversion into the bis-BOC derivative, hydrogenation on Rh/C and cleavage of the BOC protecting groups.

$^1$H—NMR in DMSO-d$_6$,δ(ppm):0.76(d, 3H, J=7.5 Hz), 1.21(m, 3H), 1.43(m, 2H), 1.61(m, 1H), 1.89(m, 1H), 2.65 (m, 2N)

EXAMPLE 17 cis-Cyclopentane-1,3-diamine (see Example 10)

88.7 g of diethyl 2,3-diazabicyclo[2.2.1]heptane-2,3-dicarboxylate (prepared according to P. G. Gassman and K. T. Mansfield, Organic Synthesis 49, 1–6) are reduced with 16.8 g of sodium in 150 ml of tetrahydrofuran and 1.5 l of liquid ammonia. After the addition of 39.2 g of ammonium chloride the ammonia is evaporated and the residue is taken up with 250 ml of dichloromethane and 250 ml of 2N hydrochloric acid. The aqueous phase is separated, back-washed with two 50 ml portions of methylene chloride and the organic phases are combined and evaporated to dryness. The residue is recrystallized from 600 ml of toluene and 300 ml of hexane. 78 g of cis-cyclopentane-1,3-diamine bis-ethylcarbamate (m.p.:110°–111° C.) are obtained.

33 g of the bis-carbamate are boiled under reflux in 1 l of 33% HBr in glacial acetic acid for 5 hours. The separated product is filtered off under suction and washed with five 50 ml portions of acetone. 27.8 g of cis-cyclopentane-1,3-diamine dihydrobromide (m.p.>250° C.) are obtained.

Elementary analysis:$C_5H_{12}N_2$.2HBr
Calculated:: C 22.92%, H 5.39%, Br 61.00%, N 10.69%
Found: C 23.08%, H 5.35%, Br 61.14%, N 10.63%

Example A

7-Chloroquinolin-4-yl)-[2-(7-chloroquinolin-4-yl-aminomethyl)-benzyl]-amine can be formulated as the active ingredient according to methods known per se to give pharmaceutical preparations of the following composition:

| 1. 500 mg tablets | |
|---|---|
| Active ingredient | 500 mg |
| Lactose powd. | 149 mg |
| Polyvinylpyrrolidone | 15 mg |
| Dioctyl sodiumsulphosuccinate | 1 mg |
| Na carboxymethylstarch | 30 mg |
| Magnesium stearate | 5 mg |
| | 700 mg |
| 2. 50 mg tablets | |
| Active ingredient | 50 mg |
| Lactose powd. | 50 mg |
| Microcrystalline cellulose | 82 mg |
| Na carboxymethylstarch | 15 mg |
| | 200 mg |
| 3. 100 mg capsules | |
| Active ingredient | 100.0 mg |
| Lactose powd. | 104.7 mg |
| Corn starch | 70.0 mg |
| Hydroxypropylmethylcellulose | 10.0 mg |

| | |
|---|---|
| Dioctyl sodiumsulphosuccinate | 0.3 mg |
| Talc | 12.0 mg |
| Magnesiumstearate | 3.0 mg |
| | 300.0 mg |
| 4. 500 mg suppositories | |
| Active ingredient | 500 mg |
| Suppository mass | ad 2000 mg |
| 5. 100 mg suppository | |
| Active ingredient | 100 mg |
| Medium chain triglyceride | 300 mg |
| | 400 mg |

We claim:

1. Compounds of the formula,

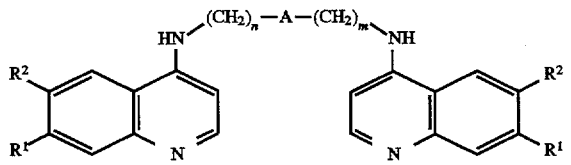

wherein $R^1$ is halogen or trifluoromethyl; $R^2$ is hydrogen or halogen; A is selected from the group consisting of cyclohexane-1,3-diyl, 2-methyl-cyclohexane-1,3,-diyl, cyclohexane-1,4-diyl, dicyclohexylmethane-4,4'-diyl, cyclopentane-1,3-diyl, phenylene-1,4, phenylene-1,3 and phenylene-1,2; n is 1 or 2; m is 1 or 2; and pharmaceutically acceptable acid addition salts.

2. The compound of claim 1, wherein $R^1$ is chlorine; A is selected from the group consisting of cyclohexane-1,3-diyl, 2 methyl-cyclohexane-1,3-diyl, cyclohexane-1,4-diyl, dicyclohexylmethane-4,4'-diyl, cyclopentane-1,3-diyl, phenylene-1,4, phenylene-1,3 and phenylene-1,2; and n and m are 1.

3. The compound of claim 1, wherein $R^1$ is chlorine and n and m are 1.

4. A pharmaceutical composition comprising a compound of the formula

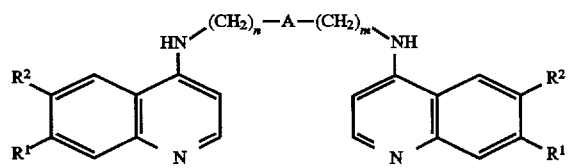

wherein $R^1$ is halogen or trifluoromethyl; $R^2$ is hydrogen or halogen; A is selected from the group consisting of cyclohexane-1,3-diyl, 2-methyl-cyclohexane-1,3-diyl, cyclohexane-1,4-diyl, dicyclohexylmethane-4,4'-diyl, cyclopentane-1,3-diyl, phenylene-1,4, phenylene-1,3 and phenylene-1,2; n is 1 or 2; m is 1 or 2; and pharmaceutically acceptable acid addition salts.

5. The pharmaceutical composition of claim 4, further comprising pharmaceutically inert, inorganic or organic carriers, preservatives, solubilizers, stabilizers, wetting agents, emulsifiers, sweeteners, colorants, flavorants, salts, buffers, coating agents and antioxidants.

6. A method for the treatment of malaria comprising administering to a patient an effective amount of a compound of the formula wherein $R^1$ is halogen or trifluoromethyl; $R^2$ is hydrogen or halogen; A is selected from the group consisting of cyclohexane-1,3-diyl, 2-methyl-cyclohexane-1,3-diyl, cyclohexane-1,4-diyl, dicyclohexylmethane-4,4'-diyl, cyclopentane-1,3-diyl, phenylene-1,4, phenylene-1,3 and phenylene-1,2; n is 1 or 2; m is 1 or 2; and pharmaceutically acceptable acid addition salts.

7. The method of claim 6 wherein the effective amount is from about 10 mg to about 2.5 g per day.

8. The method of claim 6 wherein the malaria is chloroquine-resistant.

9. The method of claim 6 wherein the malaria is chloroquine-sensitive.

10. A compound selected from the group consisting of (7-chloroquinolin-4-yl)-amine, (7-chloroquinolin-4-yl)-amine, (7-chloroquinolin-4-yl)-amine, (7-chloroquinolin-4-yl)-amine.

* * * * *

UNITED STATES PATENT AND TRADEMARK OFFICE
CERTIFICATE OF CORRECTION

PATENT NO. : 5,736,557
DATED : April 7, 1998
INVENTOR(S) : Werner Hofheinz and Werner Leupin It is certified that error appears in the above-indentified patent and that said Letters Patent is hereby corrected as shown below:

On the title page, Item [54],
Change the title to read "N,N'-BIS (QUINOLIN-4-YL)-DIAMINE DERIVATIVES, THEIR PREPARATION AND THEIR USE AS ANTIMALARIALS".

In claim 10, column 14, lines 44-47, delete
"(7-chloroquinolin-4-yl)-amine,
(7-chloroquinolin-4-yl)-amine,
(7-chloroquinolin-4-yl)-amine,
(7-chloroquinolin-4-yl)-amine."
and insert
-- (7-chloroquinolin-4-yl)-[2-(7-chloroquinolin-4-yl-aminomethyl)-benzyl]-amine,
(7-chloroquinolin-4-yl)-[3-(7-chloroquinolin-4-yl-aminomethyl)-benzyl]-amine,
(7-chloroquinolin-4-yl)-[4-(7-chloroquinolin-4-yl-aminomethyl)-benzyl]-amine,
(7-chloroquinolin-4-yl)-[3-(7-chloroquinolin-4-yl-aminomethyl)-cyclohexylmethyl]-amine. --

Signed and Sealed this

Fourteenth Day of July, 1998

*Attest:*

BRUCE LEHMAN

*Attesting Officer*     *Commissioner of Patents and Trademarks*